United States Patent [19]
Lenz et al.

[11] Patent Number: 5,527,285
[45] Date of Patent: Jun. 18, 1996

[54] DISPOSABLE INJECTION SYRINGE

[75] Inventors: Thomas Lenz, Örebro; Karlo Smit, Norsborg, both of Sweden

[73] Assignee: Funova AB, Orebro, Sweden

[21] Appl. No.: 335,719

[22] PCT Filed: May 14, 1993

[86] PCT No.: PCT/SE93/00423

§ 371 Date: Nov. 10, 1994

§ 102(e) Date: Nov. 10, 1994

[87] PCT Pub. No.: WO93/23100

PCT Pub. Date: Nov. 25, 1993

[30] Foreign Application Priority Data

May 15, 1992 [SE] Sweden .................................. 9201546

[51] Int. Cl.⁶ .................................................. A61M 5/00
[52] U.S. Cl. .................................... 604/110; 604/195
[58] Field of Search ...................... 604/110, 187, 604/218, 263, 228, 240, 208, 209, 210

[56] References Cited

U.S. PATENT DOCUMENTS

| | | | |
|---|---|---|---|
| 4,915,700 | 4/1990 | Noonan, Jr. ................ | 604/195 |
| 5,183,466 | 2/1993 | Movern ...................... | 604/110 |
| 5,221,262 | 6/1993 | Kite ........................... | 604/195 X |
| 5,250,030 | 10/1993 | Corsich ...................... | 604/218 X |

FOREIGN PATENT DOCUMENTS

| | | |
|---|---|---|
| 0326983 | 8/1989 | European Pat. Off. . |
| 89/890975 | 10/1989 | WIPO . |
| 91/12841 | 9/1991 | WIPO . |

*Primary Examiner*—John D. Yasko
*Attorney, Agent, or Firm*—Larson & Taylor

[57] ABSTRACT

Injection syringe of disposable type, including a cylinder (91), in which a piston is displaceable in and out respectively, a piston rod (3) having a press plate (12), and an injection needle (4) at the end of the syringe cylinder (1). The syringe needle (4) is mounted from inside the syringe cylinder (1) and is releasably connected (5, 9) to the syringe cylinder (1). The syringe needle (4) or the carrier (5) thereof is formed with one or more blocking ratchets (6) which cooperate with the syringe piston (2) or the piston rod (3), and which blocks the piston against being retracted after the sole injection is made, so that the syringe needle (4) becomes retracted into the inner of the syringe cylinder (1) upon withdrawal of the piston (2) after the injection has taken place.

8 Claims, 4 Drawing Sheets

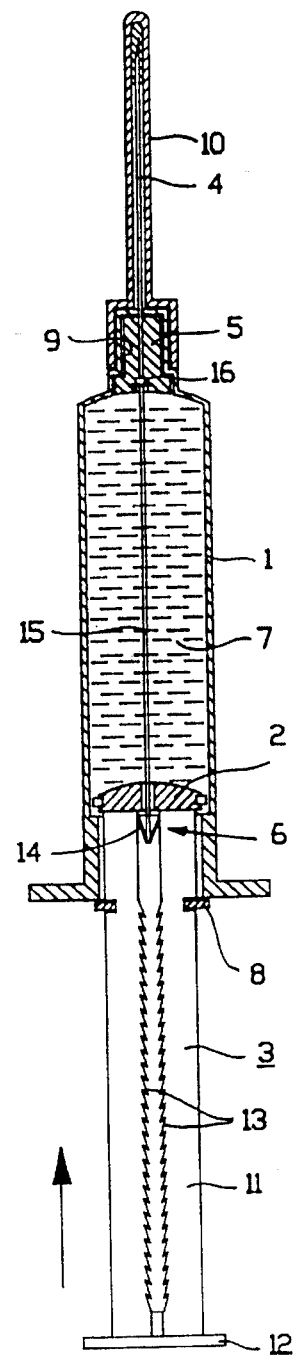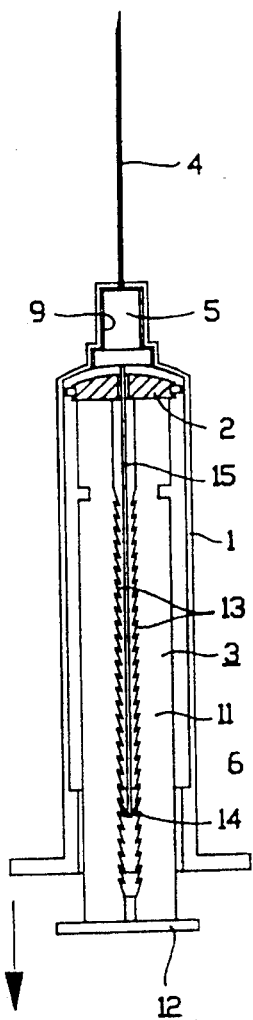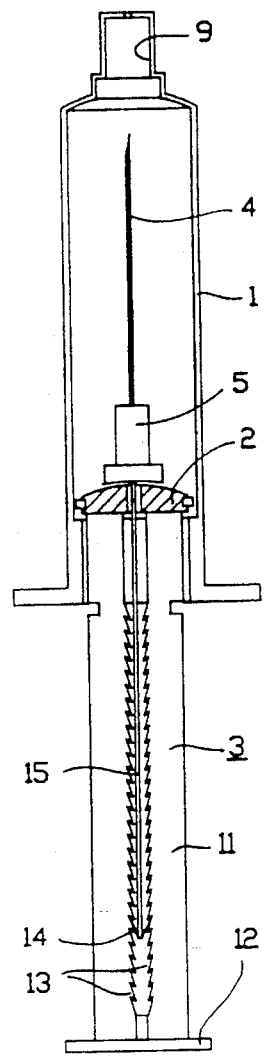
Fig. 1A
Fig. 1B
Fig. 1C

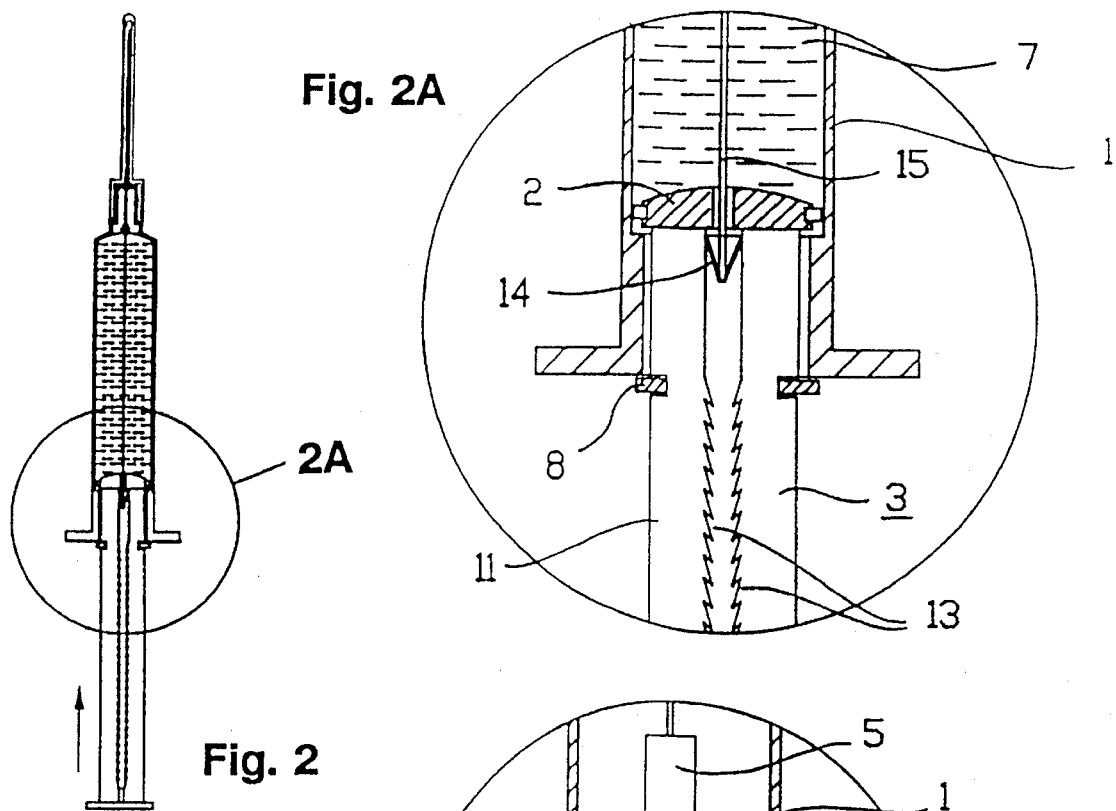
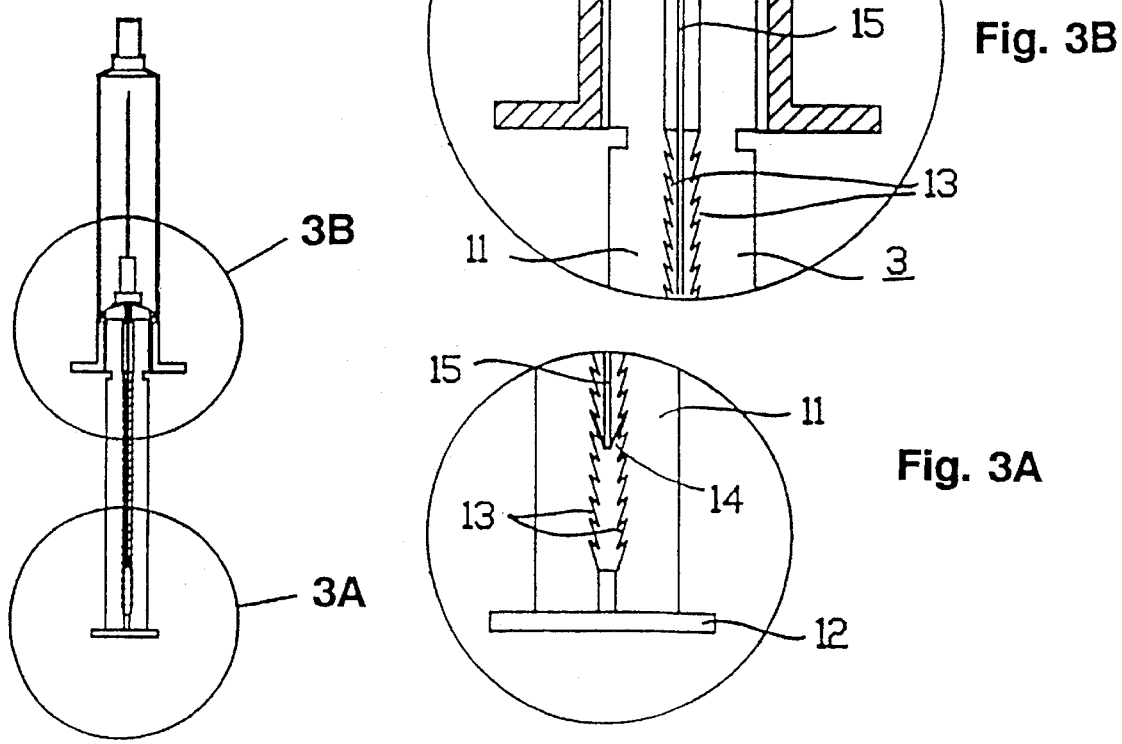

DISPOSABLE INJECTION SYRINGE

This application is a 371 of PCT/SE93/00423 filed May 14, 1993.

The present invention generally relates to a disposable injection syringe, and the invention is more particularly concerned with such a syringe which is designed such that it is made unusable for re-use after it has been used one single time, and which, in addition thereto, makes it possible to hide the injection needle tip for preventing said injection needle tip from coming into contact with any object. The invention also covers both pre-filled syringes and syringes which can filled and can be used for injection purposes—only once.

By a disposable syringe is meant, in this connection, both a prefilled syringe which can not be refilled, and a syringe which can be filled only once and can, in connection thereto, be used only once for injection purposes, and also a syringe which makes it possible to take blood samples or other types of laboratory samples only once and, in connection thereto, to expel said sample from the syringe.

The disposable syringes which are on the market to-day are mainly simple and cheap plastic copies of conventional syringes, and said known syringes are often being reused, in particular in the third world. It is also common that one and the same syringe is used by several persons within addict circles in that the syringe is lent to other persons, whereby infections are easily being transmitted from sick people to healthy people.

A few attempts have been made to provide disposable syringes which do not allow a refilling thereof. One such solution is built on the principle that the syringe piston becomes locked up in its inner position after the injection has been made, so that the syringe can not be refilled. Another solution is built on the principle that a body containing the injection medium is being deformed at the end stage of a first injection so that, also in this case, the syringe can not be refilled. Still another solution is built on the principle that the syringe piston, or any part of the syringe connected to the syringe piston, becomes broken apart, or is otherwise damaged, at the final stage of the injection process so that the connection between the piston and the active part of the piston rod is broken, whereby the syringe, also in this case, can not be refilled.

A problem with said suggested self-distroying prefill syringes and disposable syringes is that they do not allow different types of injection, and another problem is that they are formed so that the injection needle or cannula is left on the syringe after the injection. As a concequence the injection needle can be removed from the syringe and can be re-used as many times as desired thereby involving a risque of transmitting infections.

It also often happens that persons hurt themselves by stepping on injection needles which have been thrown away in the nature. Also in the medical care field accidents occur during handling of injection needles. Therefore, a further object of the invention is to suggest a prefill syringe or a disposable syringe of a type which is designed so that the injection needle or cannula is eliminated after one sole possible injection process.

Further, it is noted that injection medium bottles generally stand under a certain sub-pressure, and when filling a syringe from such a bottle it is necessary to press a slight amount of air into the bottle since it may otherwise be difficult to draw or suck the injection medium into the syringe. Therefore, a disposable syringe according to the invention preferably also should be formed so that the piston can be expelled a slight distance in connection to drawing or sucking the injection medium into the syringe.

In case of intravenous injection is is also necessary that the syringe piston can be pulled back a slight distance, whereby a slight amount of blood is being drawn into the syringe, whereby it can be checked that the injection needle has full blood contant, and this is visually confirmed by the fact that a slight amount of blood is being drawn into the syringe. Therefore a disposable syringe according to the invention preferable also should be formed so that it is possible to pull the piston a slight distance back before the very injection is started. In other words, the syringe piston should have a slight idle-movement possibility both forwardly and rearwardly in the syringe, and no blocking of the function of the syringe should be allowed during such an idle movement of the syringe piston.

According to the invention the injection needle (or cannula) is mounted from inside the syringe cylinder, and the injection needle or the carrier thereof is formed with one or more blocking means which cooperate with the syringe piston or the syringe piston rod and which block the piston against said blocking means upon each little introduction of the piston in the syringe cylinder. The injection needle or the needle carrier is formed so that the injection needle, upon an attempt to pull the piston "back" in the syringe cylinder from an introduced position, pulls the entire injection needle into a position inside the syringe cylinder, whereby neither the syringe nor the injection needle can be reused.

Further characteristics and advantages of the invention will be evident from the following detailed specification in which reference will be made to the accompanying drawings.

In the drawings

FIGS. 1A–C show a disposable syringe of the prefill type in three different function positions.

FIGS. 2 and 2A show a schematic and an enlarged detail view of the syringe according to claim 1A, and FIGS. 3, 3A and 3B show a schematic and two different enlarged details from FIG. 1C.

FIGS. 4A–D illustrate four different function positions of a fillable syringe of disposable type according to the invention.

Figure 4A:
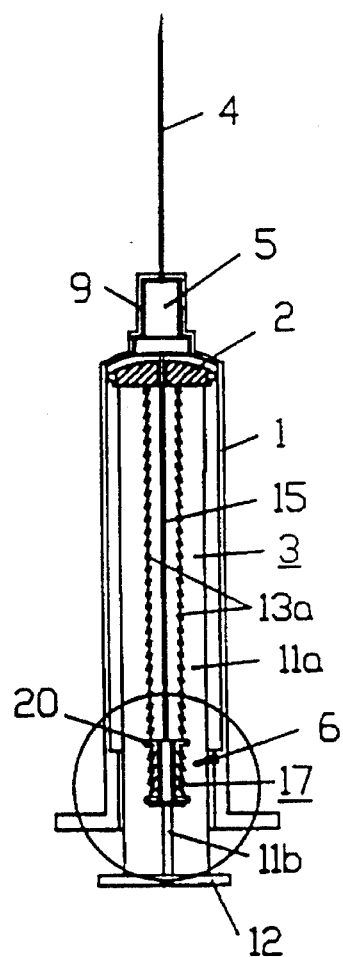

The "prefill syringe" of the disposable type shown in FIGS. 1–3 generally comprises a syringe cylinder 1, a piston 2 having a piston rod 3, an injection needle (cannula) 5 including an injection needle carrier 5 and a ratchet means 6 arranged both to make it impossible to refill the syringe and to provide a retraction of the entire injection needle into the interior of the syringe cylinder 1 after the first and sole injection has been made.

The syringe cylinder 1 and the syringe piston 2 are of conventional shape and size, and in this case the syringe is adapted to be supplied prefilled with an injection medium 7 and with the piston retracted to a far out end position, in which the piston is blocked by any type of locking means, for instance by a locking ring 8 which engages the piston rod 3 and which has to be released before the piston 2 can be moved inwards in the cylinder 1.

The injection needle (cannula) is fixedly connected to the syringe needle carrier 5 and the needle carrier 5 is, from the interior of the cylinder, introduced in a pin-shaped cavity 9 provided at the inner end of the cylinder 1. The needle carrier 5 is kept in the cavity 9 by a friction engagement and with the injection needle 4 projection through a bore at the end of the cavity 9. The connection strength between the needle carrier 5 and the cylinder cavity 9 should be such that the needle carrier 5 with the injection needle 4 can easily be pulled out of the cavity 9 and can be drawn inside the cylinder 1 after the sole injection is finished. As conventional the injection needle is protected by a protection cover 10.

The piston rod may be hollow, but in the illustrated case the piston rod 3 is formed with several, preferably four piston rod legs 11 which with one end thereof are fixed to the piston 2 and which with the opposite end are interconnected by a press plate 12 belonging to the piston rod 3. The inner edges of the piston rod legs 11 which are facing each other are formed with pawls or barbs 13 (ratchets) arranged to cooperate with the ratchet means 6 which in the illustrated case is a spring yoke 14 mounted at the end of a pull rod 15 which, with the opposite end thereof is connected to the injection needle carrier 5, for instance by means of a cross pin 16. The spring yoke 14 can be formed as a circular spring disc or a pair of spring legs which, with the free ends thereof, are facing the piston 2. The portion of the piston rod legs 11 located adjacent the piston 2 have no barbs. In the initial position the spring yoke 14 is positioned closest to the piston 2 at said smooth portion of the piston rod legs 11, so that the piston can be pressed a slight distance to the inner of the cylinder and can thereafter be pulled out a slight distance without the spring yoke 14 locking itself against the barbs 13. This possibility of moving the pistone a slight distance in and out is useful for instance for introducing a slight amount of blood into the syringe before an intravenous injection is started.

The function of the apparatus is as follows:

In the situation shown in FIG. 1A the protection cover 10 is removed; the locking ring 8 is removed; and the piston 2 is pressed inwards so that the entire injection needle 4 is filled with injection fluid. As mentioned earlier, and as most clearly shown in the detail figure part of FIG. 2A, the piston 2 can be pressed a slight distance inwards and can thereupon be pulled outwards without having the ratchet means 6 getting into operation. After the piston 2 has been pressed in a predetermined length the spring yoke 14 starts ratching over the barbs 13, whereby the piston is effectively prevented from being pulled back, see the lower detail picture of FIG. 3A.

When the injection is ended, which can be after the entire syringe has been emptied, as shown in FIG. 1B, or after only a part of the injection medium has been injected, or in any intermediate position, the piston rod 3 is withdrawn. Also the injection needle carrier 5 together with the injection needle 4 are thereby pulled rearwardly and out of the cavity 9 actuated by the spring yoke 14 and the pull rod 15, and the entire injection needle 4 is pulled to a position in the inner of the syringe as shown in FIG. 1C and the upper detail picture of FIG. 3B.

There is also a possibility of designing the injection needle and the needle carrier so that needle 4 places itself obliquely as soon as it enters the cylinder, whereby it will be quite impossible of forcing the injection needle out through the little bore at the end of the cylinder cavity 9.

Figure 4B:
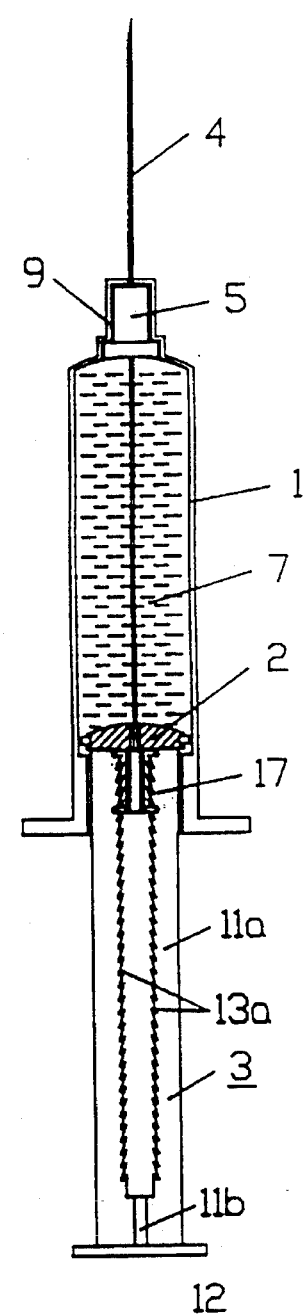
Figure 5:
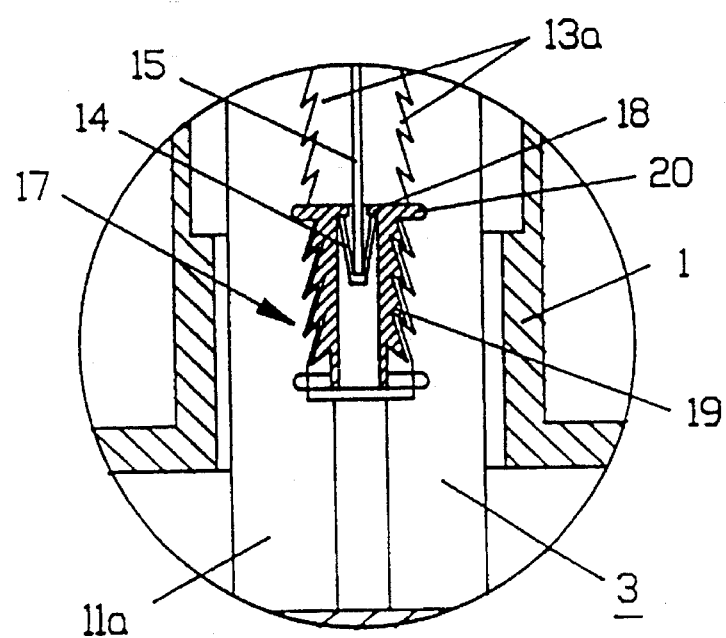
FIG. 5 is an enlarged view of the encircled detail of FIG. 4A.
Figure 6:
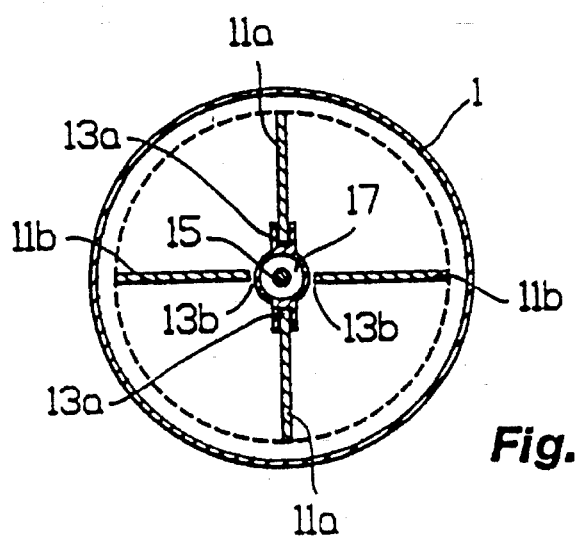
FIG. 6 is a cross section along line VI—VI of FIG. 4C.

FIGS. 4–6 show a fillable, disposable syringe according to the invention. This syringe is basically of the same type as the syringe of FIGS. 1–3, but it differs therefrom in that it has a double ratchet function which, in a first stage, makes it possible to draw up and fill the syringe with injection medium and, in a second stage, to inject said medium, whereupon a renewed retraction of the piston rod makes the injection needle with the needle carrier become retracted into the inner of the syringe cylinder as described above, so that the syringe can not be reused, and so that the injection needle is eliminated.

The double ratchet system is formed by an outer, hollow ratchet cylinder 17 which is its initial position is located as far out as possible on the piston rod 3, adjacent the press plate 12, and which at the inner thereof encloses the previously described spring yoke 14 in a position adjacent the end of the ratchet cylinder 17 facing the piston 2. This arrangement makes it possible to pull the piston outwards and thereafter press the piston back a little distance without having the ratchet function. The ratchet cylinder 17 has an end landing 18 facing the piston 2 which prevent the ratchet cylinder 17 from passing the spring yoke 14 and releasing same when the piston 2 is being retracted. On the contrary the spring yoke 14 can be moved out of the ratchet cylinder 17 in the opposite direction, and this happens when the piston 2 is pressed into the cylinder 1 as shown in FIG. 4C.

Figure 4C:
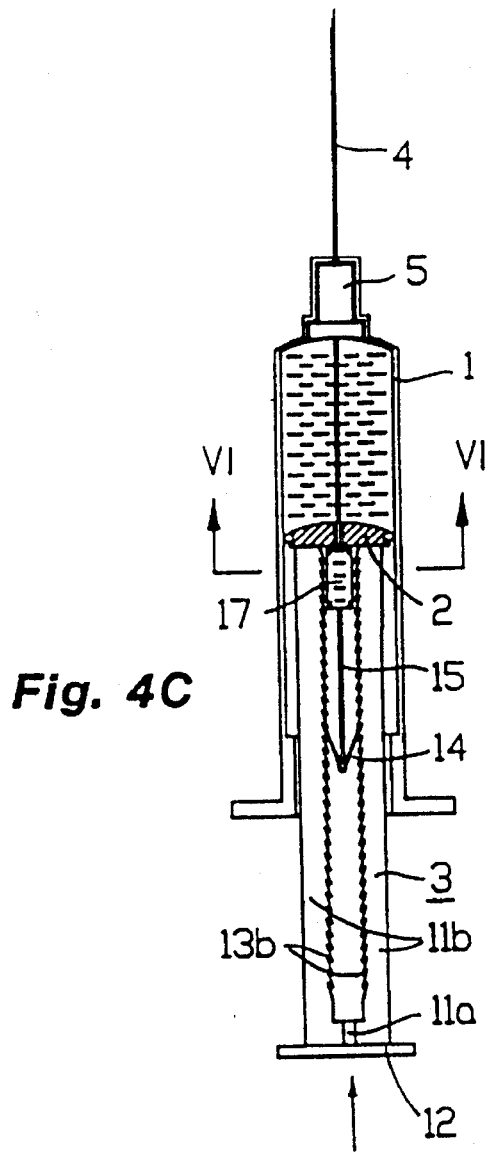
Figure 4D:
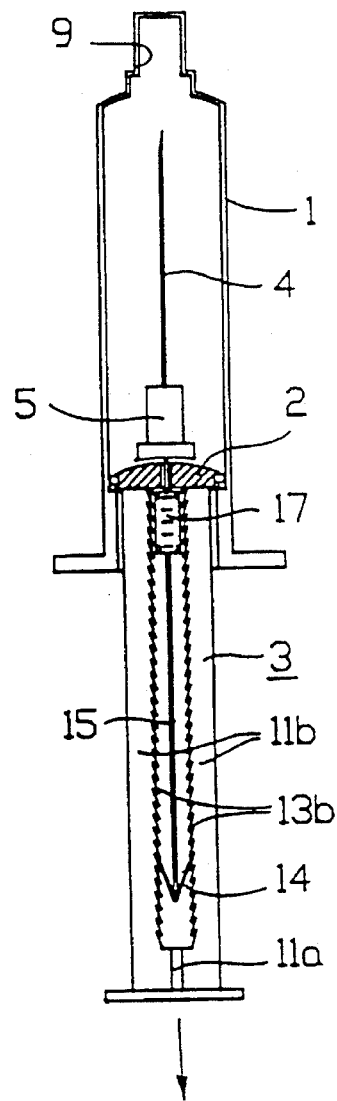

In the arrangement illustrated in FIG. 4 the piston rod legs 11 are, in pairs, formed with two different types of barbs 13a and 13b respectively as shown in FIGS. 4A–B and 4C–D respectively. In FIGS. 4C–D the piston is rotated 180° about a longitudinal axis as compared with the position shown in FIGS. 4A–B. Two opposite legs 11a have barbs 13a which allow a retraction of the piston rod 3 with the piston 2 under successive ratchet contact between the ratchet cylinder 17 and the barbs 13a, and the two other opposite legs 11b have barbs 13b which allow a pressing inwards of the piston 2 under successive ratchet contact between the spring yoke 14 and the barbs 13b. In other words the barbs 13 only allow a retraction of the piston, and the barbs 13b only allow an introduction of the piston 2 in the syringe cylinder 1.

To this end the ratchet cylinder 17 is, along two opposite generatixes coinciding with the barbs 13a, formed with formed with barbs (pawls) or ratchets 19 arranged to lockingly engage the barbs 13a, whereas the ratchet cylinder is smooth along the remaining parts thereof, so that is can slide over the barbs 13b of the two other opposited piston rod legs 11b. For keeping the ratchet cylinder in a correct rotational position it is formed with radially projecting guide arms 20 which engage the legs 11a.

In the initial position, which is shown in FIG. 4a and in the detail of FIG. 5, the piston 2 in fully introduced in the cylinder 1, the ratchet cylinder 17 is positioned adjacent the press plate 12 of the piston rod 3, and the spring yoke 14 is positioned closest to the inner landing 18 of the ratchet cylinder 17. In this position the piston can be retracted a slight distance and can thereafter be introduced in the syringe cylinder 1 without being blocked. This is an important feature, for instance for pressing air into an injection medium bottle and for drawing up injection fluid into the syringe.

FIG. 4B shows how injection medium has been sucked up in the syringe. This is possible since the spring yoke 14 with the free ends thereof is biassed against the upper landing edge 18 of the ratchet cylinder 17 and keeps the ratchet cylinder 17 in a position adjacent the outer end of the syringe cylinder 1. Thereby the barbs 19 of the ratchet cylinder 17 snap over the barbs 13a of the piston rod legs 11a as illustrated in FIGS. 4A and 4B, whereas said ratchet cylinder 17, with the smooth side portions pass inside the tops of the barbs 13b of the two opposite piston rod legs 11b. In its end position the ratchet cylinder 17 is in contact with the bottom surface of the piston 2, which position is shown in FIGS. 4C and 4D. It should be noticed that the sucking or drawing up injection medium can be ended with the ratchet cylinder 17 in any intermediate position between the defined end positions.

When injection medium has been drawn up in the syringe the piston 2 is pressed in. The ratchet cylinder 17 is blocked by the barbs 13a in relation to the piston 2 and therefore follows the movement of the piston 2. The spring yoke 14, which is blocked in relation to the injection needle carrier 5 via the pull rod 15, is thereby moved out of the ratchet cylinder 17 and starts snapping over the barbs 13b along the piston rod legs 11b. Said barbs 13b allow an introcution of the piston 2 and thereby an injection of the injection medium in the syringe, but they prevent a refilling of the syringe. This function is shown in FIG. 4C.

When the injection process is ended the piston rod 3 is withdrawn as shown in FIG. 4D, whereby the injection needle 4 and the needle carrier 5 are withdrawn into the inner of the syringe cylinder.

REFERENCE NUMERALS 1 syringe cylinder
2 syringe piston
3 piston rod
4 injection needle (cannula)
5 injection needle carrier
6 ratchet means
7 injection medium
8 locking ring
9 cavity
10 protection cover
11 piston rod legs
12 press plate (of 3)
13 barbs
14 spring yoke
15 pull rod
16 cross pin
17 ratchet cylinder
18 landing
19 barbs
20 guide arms

We claim:

1. Injection syringe of disposable type and comprising a cylinder (1) in which a piston (2) is movable inwards and outwards respectively, a piston rod (3) having a press plate (12), and an injection needle (4) at the end of the syringe cylinder (1), in which the injection needle (4) is mounted from inside the syringe cylinder (1) and is releasable at its mounting place (5, 9) in the syringe cylinder (1), and having a co-operating means (13, 14) for retracting said injection needle (4) into the cylinder (1) upon withdrawal of the piston rod (3), characterized in that the injection needle (4) or the carrier (5) thereof is formed with one or more blocking means (13) which cooperates(s) with interengaging means (14) of the syringe piston (6) or the syringe piston rod (3), said blocking and interengaging means (13, 14) being in the form of barbs (13a, 13b) and ratchet like parts (14, 15) which lockingly engage in the retraction direction, and which block the piston (2) against said blocking means (13) upon any little introduction of the piston (2) in the syringe cylinder (1) so that the injection needle (4), upon any attempt to pull the piston "back" in the syringe cylinder from an introduced position, pulls the injection needle (4) into a position inside the syringe cylinder.

2. Injection syringe according to claim 1, characterized in that the piston rod is hollow, or is formed with one or more pairs of piston rod legs (11a, 11b) which along the edges thereof facing each other has barbs (13a, 13b) extending along at least the largest part of said piston rod legs.

3. Injection syringe according to claim 1, characterized in that the ratchet means (6) comprises a pull rod (15) which is fixedly connected to the injection needle (4) or to the needle carrier (5), and which, at the free end thereof, has a ratchet means (14) which cooperates with some part (13) of the piston rod (3) thereby allowing an introduction of the piston rod (3) into the syringe cylinder (1) but not a free withdrawal of the piston rod out of the cylinder (1).

4. Injection syringe according to claim 1, characterized in that the ratchet means (14) at the end of the pull rod (15) comprises one or more spring arms which, with the free ends thereof, are facing the needle end of the syringe, and which cooperates(s) with barbs (13) on the piston rod (3), which barbs (13) are arranged with the locking barb portion thereof facing the injection needle end of the syringe and with the trailing end facing the free end of the piston rod (3).

5. Injection syringe according to claim 1, characterized in that the piston rod or the piston rod legs (11) are smooth and have no barbs (13) along a little length thereof as seen from the piston (2) and back therefrom, and in that the ratchet means (14) at the end of the pull rod (15) is arranged to be positioned closest to the piston (2) at said barb free portion when the piston rod (3) is in position for injection.

6. Injection syringe according to claim 1, characterized in that the blocking means is a double function means which allows a sole time filling of the syringe with injection medium, or a sole time taking of samples and an sole time injection and an sole time expelling of the laboratory sample respectively and which comprises an outer ratchet cylinder (17) which, along one side thereof or along two opposed generatrixes, has pawls or barbs (19) which cooperate with equivalent pawls or barbs (13a) on the piston rod (3) and which allow a free withdrawal of the piston (2) a sole time only, and a spring yoke (14) which, with the free ends of its spring arms facing the piston (2) cooperate with other pawls or barbs (13b) on the piston rod (3), which allow a free introduction of the piston into the cylinder (1) but which, upon withdrawal of the piston (2) makes the injection needle (4) become retracted into the inner of the cylinder (1).

7. Injection syringe according to claim 6, characterized in that the barbs (13a) on the piston rod (3) which cooperate with the outer ratchet cylinder (17) are arranged with the locking edges thereof directed oppositely to the piston (2) and with the trailing edges thereof facing a piston (2), so that the ratchet cylinder (17) can be moved from a initial position spaced from the piston (2) to an end position adjacent the piston (2), whereas those barbs (13b) which cooperate with the spring yoke (14) are directed oppositely.

8. Injection syringe according to claim 6, characterized in that the ratchet cylinder (17) in its initial position is located adjacent the outer end (12) of the piston rod (3), and in that the spring yoke (14) at the end of the pull rod (15), in its initial position, is located inside the ratchet cylinder (17) at the innermost end thereof.

* * * * *